United States Patent
Peeters et al.

(10) Patent No.: US 7,087,633 B2
(45) Date of Patent: *Aug. 8, 2006

(54) METHOD FOR TREATING PERINATAL ASPHYXIA IN A HUMAN OR ANIMAL NEONATE

(75) Inventors: Cacha Marie Pétronelle Cathérine Dorotheé Peeters, Utrecht (NL); Floris Groenendaal, Houten (NL); Frank Van Bel, Amstelveen (NL)

(73) Assignee: Universitair Medisch Centrum, Utrecht (NL)

( * ) Notice: Subject to any disclaimer, the term of this patent is extended or adjusted under 35 U.S.C. 154(b) by 13 days.

This patent is subject to a terminal disclaimer.

(21) Appl. No.: 10/889,058

(22) Filed: Jul. 13, 2004

(65) Prior Publication Data

US 2005/0009915 A1    Jan. 13, 2005

Related U.S. Application Data

(63) Continuation-in-part of application No. 10/362,051, filed as application No. PCT/NL01/00266 on Mar. 30, 2001, now Pat. No. 6,894,069.

(30) Foreign Application Priority Data

Mar. 31, 2000    (EP) .................. 00201191

(51) Int. Cl.
*A61K 31/4168*    (2006.01)

(52) U.S. Cl. ..................................... 514/398

(58) Field of Classification Search ..................... None
See application file for complete search history.

(56) References Cited

U.S. PATENT DOCUMENTS

| 5,464,858 A | 11/1995 | Griffith et al. .............. 514/399 |
| 5,854,234 A | 12/1998 | Hansen et al. .............. 514/212 |

FOREIGN PATENT DOCUMENTS

WO    WO 94/12165    6/1994

OTHER PUBLICATIONS

K.J. Escott et al., "Cerebroprotective effect of the Nitric Oxide Synthase Inhibitors, 1-(2-trifluoromethylphenyl) imidazole and 7-nitro indazole, afeter transient focal cerebral ischemia in the rate", Journal of Cerebral Blood Flow and Metabollism, 1998, pp. 281-287, XP-001008675.

E. Dzoljic et al., "Anticonvulsant activity of new and potent inhibitors of nitric oxide synthase", Brian Re. Bull., 1997, pp. 191-195, XP-001008673.

J.P. Bolanos et al., "Roles of Nitric Oxide In Brain Hypoxia-Ischemia", Biochimica et Biophysica ACTA, 1999, pp. 415-436, XP-00937744.

K. Kumar, "Hypoxic-Ischemic Brian Damage In Perinatal Age Group", Indian Journal of Pediatrics, 1999, pp. 475-482, XP-000937788.

*Primary Examiner*—Phyllis G. Spivack
(74) *Attorney, Agent, or Firm*—Young & Thompson

(57) ABSTRACT

A method for treating perinatal asphyxia is disclosed comprising administering 2-iminobiotin or a salt or ester thereof.

4 Claims, 3 Drawing Sheets

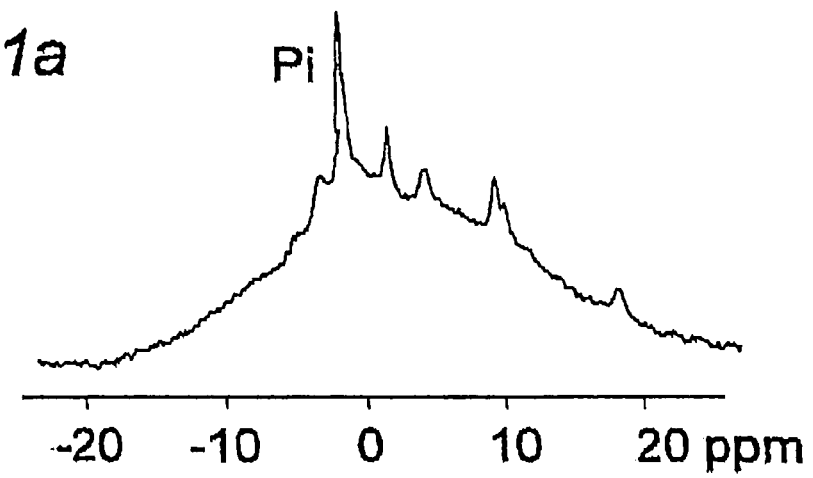
PLAC at 24 h post HI
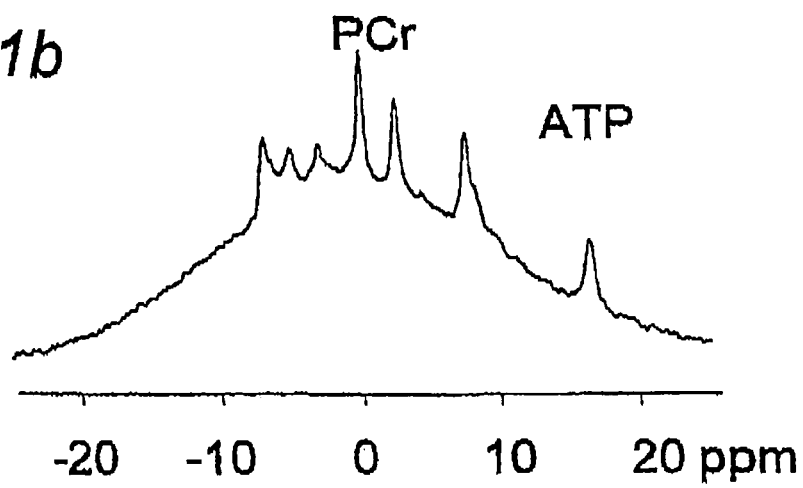
2-IB at 24 h post HI

METHOD FOR TREATING PERINATAL ASPHYXIA IN A HUMAN OR ANIMAL NEONATE

CROSS REFERENCE TO RELATED APPLICATIONS

This application is a continuation-in-part of application Ser. No. 10/362,051, filed on Jul. 10, 2003 now U.S. Pat. No. 6,894,069. application Ser. No. 10/362,051 is the national phase of PCT International Application No. PCT/NL01/00266 filed on Mar. 30, 2001 under 35 U.S.C. § 371, which claims the priority of Europe Application 00201191.4, filed on Mar. 31, 2000. The entire contents of each of the above-identified applications are hereby incorporated by reference

FIELD OF THE INVENTION

The present invention relates to pharmaceutical compositions that can be used to prevent and/or treat, in newborn babies, the effects of complications that may occur during childbirth.

In particular, the invention relates to pharmaceutical preparations that can be used to prevent and/or treat, in newborn babies, the effects of perinatal asphyxia (=hypoxia-ischemia).

Specifically, the invention relates to pharmaceutical preparations that can be used to prevent and/or treat, in newborn babies, brain damage or brain injury that may result from complications during childbirth such as perinatal asphyxia and/or hypoxia-ischemia.

It is envisaged that the preparations of the invention may also be used for veterinary purposes, e.g. to prevent and/or treat the effects of complications—such as those mentioned above—that may occur during the birth of any animal. For instance, it is known that up to 15% of young livestock before the age of weaning may die from asphyxiation. Thus, in another aspect, the invention provides veterinary preparations.

It is also envisaged that the invention may be used to prevent and/or treat, in people of all ages, the complications and (after-)effects that occur during an insult from for instance brain cell injury. Thus, in yet another aspect, the invention also provides suitable pharmaceutical compositions for the treatment of such complications and/or (after-) effects.

BACKGROUND

Perinatal asphyxia is a serious complication of childbirth, which affects about 1% of newborns world-wide. It may lead to hypoxia-ischemia or more generally to injury to the baby due to lack of (sufficient) oxygen.

In particular at risk of such damage is the brain. For instance, hypoxia-ischemia during childbirth may result in neonatal encephalopathy, cerebral palsy, mental retardation, learning disabilities, epilepsy or other long-term effects. For a large part, these effects are caused by excessive formation of free radicals such as superoxide and hydroxyl radicals. These radicals are especially formed directly after a period of hypoxia-ischemia when reoxygenation and reperfusion are re-established. Together with NO (nitric oxide) superoxide reacts to peroxynitrite, which attacks the brain cell membranes, resulting in lipid peroxidation and eventually cell death.

It has been suggested in the art to prevent or treat the above effects by administering, to neonates that are at risk, free radical scavengers and/or xanthine oxidase inhibitors such as allopurinol ("ALLO") or non-protein bound iron chelators such as deferoxamine ("DFO"). In a pilot study in newborn babies and in experimental studies it has been shown that allopurinol and deferoxamine reduce free radical-induced brain damage in newborns to some extend, these compounds, however, are still not fully satisfactory.

Since excessive biosynthesis of NO results in perinatal destruction of neurons, the use of nitric oxide synthase inhibitors seems to be promising in reducing brain injury after perinatal hypoxia-ischemia. However, data concerning non-specific NOS inhibitors after hypoxia-ischemia are conflicting: for instance it has been shown that $N^G$-nitro-L-arginine (NNLA) compromised cerebral energy status during and after hypoxia-ischemia (HI) in newborn piglets (Groenendaal et al, *Pediatric Res.* 45 (1999) 827–833), whereas L-nitro-arginine methyl ester (L-NAME) was neuroprotective in neonatal rats (Palmer et al., *Pediatric Res.* 41 (1997) 294A). Nowadays, three types of NOS isoforms have been characterised: neuronal, inducible and endothelial NOS. Using selective NOS inhibitors and transgenic animals it has been suggested that the NOS isoform determines whether it acts neuroprotective or neurotoxic upon HI (Bolaños and Almeida, *Biochim. Biophys. Acta* 1411 (1999), 415–436). Johnston et al (*Semin. Neonatal.* 2000(5): 75–86) showed that 7-nitroindazole, mainly a neuronal NOS inhibitor but only injectable intraperitoneally, was effective in reducing apoptosis and reducing the levels of citrulline. Higuchi et al (*Eur. J. Pharmacology* 342 (1998) 47–49) and Tsuji et al (*Pediatric Res.* 47 (2000), 79–83) reported that aminoguanidine, mainly an inducible NOS inhibitor, reduced infarct volumes in neonatal rats. On the other hand, endothelial NOS knock-out mice were highly sensitive to cerebral ischemia, suggesting a role for eNOS in cerebral perfusion. NOS inhibitors with potential usefulness in reducing brain injury after perinatal HI need to be water-soluble for rapid intravenous injection in mother or newborn child/animal and need to be transported to the brain and be selective inhibitive for neuronal and inducible NOS.

Until now no accepted therapy is available for asphyxiated infants. Therefore, there is a need for pharmaceutical preparations that may be used to prevent and/or treat, in newborn babies, the effects of complications that may occur during childbirth.

In addition, as already mentioned above, there is also a need for veterinary preparations that can be used for the same or similar purposes is newborn animals or to improve growth after birth. Also, there is a need for pharmaceutical preparations that can be used to prevent and/or treat (the effects of) brain cell injury in people of all ages.

DESCRIPTION OF THE INVENTION

According to the present invention, it has been found that 2-iminobiotin and other specific neuronal and inducible NOS inhibitors, can be used to prevent and/or treat the above-mentioned effects. In particular, in in vivo studies involving piglets (vide the Experimental Part below), it was found that 2-iminobiotin is more effective in preventing and/or treating these effects than either allopurinol and/or deferoxamine, e.g. about 60% more effective then placebo treatment and about 25% more effective than treatment with allopurinol and/or deferoxamine.

Therefore, the NOS inhibitors to be used according to the present invention should be capable of inhibiting neuronal NOS (nNOS=brain NOS), as well as inducible NOS (iNOS). However, the NOS inhibitor should not significantly inhibit endothelial NOS (eNOS). Specifically, the inhibiting effects on nNOS and on iNOS should correspond to an inhibitory concentration $IC_{50}$ of 150 µM or lower, preferably 50 µM or lower, whereas the inhibiting effect on eNOS, if any, should correspond to an inhibitory concentration $IC_{50}$ of 250 µM or higher, preferably 500 µM or higher. In particular the inhibitory concentration of either nNOS or iNOS or both should be at least a factor 5, preferably at least a factor 50 lower than the inhibitory concentration on eNOS.

The inhibitor is preferably highly soluble in aqueous medium. In general the solubility should be such that a prophylactically or therapeutically effective amount of the inhibitor is soluble in 100 ml or less, preferably in 50 ml or less aqueous medium for newborn babies. In particular the inhibitor has a solubility in aqueous medium of at least 50 µmol per 100 ml, preferably at least 150 µmol per 100 ml.

It was found that 2-iminobiotin and other nNOS, iNOS, non-eNOS inhibitors such as S-benzylisothiourea, L-thiocitrulline, $N^G$-monoethyl-L-arginine, TRIM (1-(2-trifluoromethylphenyl)imidazole), meet the requirements of sufficient specificity and solubility.

Thus, in a first general aspect, the invention relates to a pharmaceutical composition, comprising a NOS inhibitor such as 2-iminobiotin or a pharmaceutically acceptable salt or ester thereof, and optionally at least one pharmaceutically acceptable carrier, excipient or adjuvant. Pharmaceutically acceptable salts comprise e.g. alkali metal salts, alkaline earth metal and zinc salts, ammonium and substituted ammonium salts. Pharmaceutically acceptable esters comprise e.g. lower alkyl esters, such as methyl, ethyl, and isopropyl esters, hydroxyalkyl esters, benzyl esters, and the like. Wherever reference is made herein to (2-)iminobiotin, such salts and esters are understood to be included.

In a first specific aspect, the invention relates to a pharmaceutical composition for the prevention and/or treatment in neonates of the effects of complications during childbirth, said preparation comprising a selective NOS inhibitor as defined above, and optionally at least one pharmaceutically acceptable carrier, excipient or adjuvant.

In particular, this aspect of the invention relates to such a pharmaceutical composition for the prevention and/or treatment in neonates of the effects and consequences of perinatal asphyxia (=hypoxia-ischemia); for the prevention and/or treatment in neonates of brain injury or brain damage following complications during birth, including but not limited to neonatal encephalopathy, cerebral palsy, mental retardation, learning disabilities and epilepsy; and/or for the prevention and/or treatment in neonates of a reduction in cerebral energy status and/or a reduction in electrical brain activity following complications during birth, lactate formation (metabolic acidosis), low apgar scoring scale during childbirth.

In a second specific aspect, the invention relates to the use of the selective NOS inhibitor, such as 2-iminobiotin or a pharmaceutically acceptable salt or ester thereof, in the preparation of a pharmaceutical composition for the prevention and/or treatment, in neonates, of the effects of complications during childbirth as described above.

In another specific aspect, the invention relates to a pharmaceutical composition for the prevention and/or treatment of (the effects of) brain cell injury in people of all ages, said preparation comprising an inhibitor as described above, and optionally at least one pharmaceutically acceptable carrier, excipient or adjuvant, and to the use. Brain cell injury may be associated with focal ischemia, thrombotic stroke, global ischemia, neurodegeneration, such as in neurodegenerative diseases like Alzheimer's disease and Parkinson's disease, infections such as meningitis, traumatic brain injury and sub-arachnoidal hemorrhage. Also, the invention relates to the use of 2-iminobiotin or related selective NOS inhibitor or a pharmaceutically acceptable salt or ester thereof in the preparation of a pharmaceutical composition for the prevention and/or treatment of (the effects of) brain cell injury in people of all ages.

In another general aspect, the invention relates to a veterinary composition, said preparation comprising a selective inhibitor as described above and optionally at least one carrier, excipient or adjuvant acceptable for veterinary purposes.

In a further specific aspect, the invention relates to a veterinary composition for the prevention and/or treatment in newborn animals of the effects of complications during the birth of such an animal, said preparation comprising the inhibitor, and optionally at least one carrier, excipient or adjuvant acceptable for veterinary purposes and to their use in the preparation of a veterinary composition for the prevention and/or treatment in newborn animals of the effects of complications during the birth of such an animal and for stimulating growth of an animal before and after birth.

The term "selective NOS inhibitor" in the context of the present invention means a compound capable of inhibiting inducible nitric oxide synthase (iNOS) as well as neuronal nitric oxide synthase (nNOS) but not or much less strongly inhibiting endothelial form of nitric oxide synthase (eNOS), as defined above.

The term "complications during childbirth" includes any irregularity or complication that may occur—and/or that may have occurred—during childbirth and that may cause harm to the newborn, including but not limited to those irregularities or complications that may occur prior to childbirth, while the baby is being born, or shortly thereafter; and irrespective of the cause(s) thereof (e.g. with the baby itself and/or with the mother).

In particular, the term "complications during childbirth" includes any such irregularities/complications that may lead to—or that may put the baby at risk of—asphyxiation (=hypoxia, ischemia or generally lack of sufficient supply of oxygen to the baby) and/or to any tissue or organ of the baby; and/or any such irregularities or complications that may lead to brain damage or brain injury in the baby or that put the baby at risk thereof. These may include complications such as mental retardation, neonatal encephalopathy, learning disabilities and epilepsy.

Thus, in particular, the pharmaceutical preparation of the invention may be used to prevent and/or treat, in neonates, the effects of perinatal asphyxia (=hypoxia-ischemia); to prevent and/or treat, in neonates, brain injury or brain damage following complications during birth, including but not limited to neonatal encephalopathy, cerebral palsy, mental retardation, learning disabilities and epilepsy; and/or to prevent and/or treat, in neonates, a reduction in cerebral energy status and/or a reduction in electrical brain activity following complications during birth.

With respect to the above and the further disclosure herein, it will be clear to the skilled person that in or for those aspects wherein the invention relates to veterinary preparations and/or veterinary uses of (the compositions containing) the appropriate iNOS and nNOS inhibitor, the above applies analogously, e.g. by reading (newborn) animal instead of (newborn) baby/child and by reading mother of the (newborn) animal instead of mother of the (newborn) baby or child.

The pharmaceutical compositions of the invention are intended to be administered to newborn babies, and in particular to neonates that suffer from, are expected to suffer from, or are otherwise judged to be at risk from the above-mentioned effects. Also, the pharmaceutical composition can be administered to the mother of the fetus, when an asphyxiated newborn is expected. For the purposes of the present invention, the terms "newborn baby" and "neonate" include babies born by natural childbirth as well as babies that have been delivered by for instance caesarean section, and also include babies that have been born prematurely and/or the birth of which has been artificially induced. The term mother refers to the mother of the fetus or the newborn baby, including natural, inseminated, induced and carrier mothers.

Analogously, the veterinary preparations/compositions of the invention are intended to be administered to newborn animals, especially mammals, such as piglets, lambs, calves, horses, goats, and newborn pets, such as cats and dogs etc., or to the mother animals, also in the case of poultry.

Whether any newborn baby is at risk of any of the above effects—or more generally whether treatment with the compositions of the invention is indicated—will usually be determined by the clinician, taking into account any complications and/or irregularities that may have occurred shortly before or during childbirth. Babies at risk may be determined by decelerations in the fetal heart rate patterns or in the cardio-tocogram (CTG), meconium-stained amniotic fluid, metabolic acidosis in microblood samples and loss of fetal movement or other symptoms known to the skilled obstetrician. Furthermore, fetuses that experience placental insufficiency and intra-uterine growth retardation have an increased risk of complications. Also, after birth, babies subjected to perinatal asphyxia may be identified by ascertaining the presence of (biphasic) changes in brain activity or brain energy level, for instance using magnetic resonance techniques, including but not limited to those described in the Experimental Part below; but also by lactate values in blood, low Apgar scores, blood gas values, the clinical condition and the electro-encephalogram (EEG). Alternatively, any fetus can be considered as being at risk of suffering from birth complications such as asphyxia, and preventive administration can therefore be indicated generally.

Usually, treatment of a neonate with the compositions of the invention will be carried out shortly after childbirth, e.g. during the "window" for therapeutic intervention. Usually, this window spans the first day following childbirth, and in particular the first 3–24 hours following childbirth. However, if an asphyxiated baby can be expected, treatment will be carried out in the mother before the expected labour, in particular about 24 h before labour or during the antenatal phase of placental insufficiency and growth retardation, or even longer before expected delivery, e.g. up to 4 or even 8 weeks before expected delivery.

As part of such treatment, the preparations of the invention will generally be administered to the neonates in one or more pharmaceutically effective amounts, and in particular in one or more amounts that are effective in preventing and/or treating the above-mentioned effects. Such treatment may involve only single administration of a composition of the invention, but usually—and preferably—involves multiple administrations over several hours or days, e.g. as part of or according to an administration regimen or treatment regimen. Such a treatment regimen may for instance be as follows: a continuous intravenous infusion from soon after birth until 24 to 48 hours after birth. In the case of preventive treatment, the treatment regimen may be given intravenously to the mother of the fetus just before the intended high-risk delivery or orally in the case of placental insufficiency and growth retardation.

Usually, the amounts of NOS inhibitor administered to the neonate will correspond to between 0.01 and 250 mg per kg body weight preferably between 0.1 and 10 mg/kg. These amounts refer to the active component and do not include carrier or adjuvant materials such as carbohydrates, lipids or proteins or the like, that may originate from the production of the active inhibitors or may be used in assisting administration or targeting. These amounts may be administered as a single dose or as multiple doses per day, or essentially continuously over a certain period of time, e.g. by continuous infusion.

Treatment may be continued up to 24 or even 48 hours after asphyxia, or otherwise until the neonate is judged no longer to be at risk of the effects mentioned above.

However, the treatment, especially the preventive treatment, may also involve administration of the appropriate NOS inhibitor to the mother before or during partition, preferably by intravenous injection. The amounts to be administered can then be the same or higher, depending on the placental transfer and the metabolism, the first pass effect in the liver and the distribution volume of the compound. Thus the amounts administered to the mother may vary between e.g. 0.01 and 250 mg, preferably between 1 and 200 mg of active component per kg of the body weight of the mother.

The inhibitors such as 2-iminobiotin can be administered to the mother when there is a risk of their baby suffering from asphyxia as explained above, or more generally when the intervention of an obstetrician is desired. Administration may also be indicated as a preventive measure to pregnant women of higher risk, e.g. to women of over a certain age, e.g. 36 years of age, women having experienced a previous perinatal sib death, women having been treated for infertility, or having placental insufficiency, intrauterine growth retardatation, chorioamnionitis, polyhydramnion or placenta praevia, women suffering of diseases such as diabetes or thyroid problems and to mothers with placental insufficiency or intra-uterine growth retardation. Iminobiotin or another inhibitor can then be given to the fetus prophylactically by administration to the mother, thus protecting the newborn against brain damage in case of asphyxia and/or by restoring intrauterine growth in case of retarded growth. The administration can be started 1–4 weeks before expected birth.

Administration to the mother in these cases can be done e.g. orally, as further illustrated below, or by intravenous or intramuscular means. Administration is preferably performed on a daily basis, preferably one dosage per day, from the moment during pregnancy when the risk is diagnosed until delivery. Intravenous or intramuscular formulations are preferably such that the active component is bio-available for extended periods, e.g. using liposomes to which iminobiotin is coupled.

Administration to gestating animals can be done as a preventive measure when there is an increased risk of birth complications or insufficient growth. Such increased risks can be indicated by relatively high perinatal morbidity or mortality of the animal breeding farm in question or of the animal race in question. The active compound, such as 2-iminobiotin, is preferably administered orally to the mother animal in these cases, in such a manner that it reaches the fetus through the placenta before birth, or through the mother milk after birth, until weaning. The active compound can be added to the animal fodder, or the special lactation fodder, or as a top dressing to be added to the normal feed or lactation feed.

Administration of 2-iminobiotin and similar inhibitors is also useful for enhancing growth before and after birth of mammals, especially in pig, cattle, horse, goat and sheep breeding. This can be effected before birth by passage through the placenta, or after birth by passage through the mother milk. For weaners, the active compound can be given in the feed for a certain period of time, e.g. 1–13 weeks after weaning. It can be given to the newborn either orally, or by intravenous, intramuscular, intracutane or intraperitoneal administration after weaning.

The preparations of the invention may contain 2-iminobiotin or other suitable inhibitors as the free compound or as a pharmaceutically acceptable salt or ester; optionally in combination with one or more pharmaceutically acceptable carrier, adjuvants and/or excipients.

The pharmaceutical preparation of the invention may be administered in any suitable manner—e.g. as known per se for allopurinol and/or deferoxamine—including but not limited to oral administration, intravenous administration, subcutaneous administration and/or intramuscular administration. Thus, the pharmaceutical preparation of the invention may be in any form suitable for such administration, including but not limited to tablets, capsules, powders, sachets, solutions, suspensions, emulsions, elixirs, droplets, sprays, etc. These may be formulated in a manner known per se, optionally using one or more suitable pharmaceutically acceptable adjuvants, excipients or carriers; and may also be suitably packaged, e.g. in a suitable container such as a vial or a bottle. Oral administration of a inhibitor of extremely low toxicity such as 2-iminobiotin can also be in the form of a nutraceutical, i.e. as a component to be incorporated in a food product such as a beverage, desserts, etc, for mothers close to the end of the pregnancy who do or do not have a specific risk for complications at birth.

Preferably, the pharmaceutical preparations of the invention are administered intravenously, such as by injection and in particular by (drip-)infusion. Preparations suitable for such intravenous administration may for instance be prepared by mixing 2-iminobiotin or a salt or ester thereof with water or a pharmaceutically acceptable buffer or solution such as normal saline. For this purpose, the pharmaceutical preparations of the invention may also be provided in a form that can be—and/or that is intended to be—dissolved or reconstituted to provide a preparation suitable for intravenous administration. For instance, the preparations of the invention may be in the form of a powder (e.g. in a vial or sachet) that is dissolved or otherwise reconstituted with water or a physiologically acceptable solution or buffer just prior to injection or infusion.

These administration forms are also suitable for the treatment or prevention of brain injuries in mammals, especially humans, of any age as described above. The administration dosages will depend on several factors, including age, seriousness of the injury, aetiology etc., and may vary from e.g. 0.1 to 250 mg per kg body weight, preferably from 1 to 100 mg per kg body weight, to be given in a single administration, or repeatedly, e.g. on a daily basis.

The pharmaceutical compositions of the invention will contain the inhibitor in a suitable amount, preferably as a unit dose; e.g. in amounts that allow for convenient administration of the doses indicated above.

Besides the 2-iminobiotin or other specific NOS inhibitor, the preparations of the invention may also contain one or more other therapeutically effective substances, and in particular one or more active substances that are suitable and/or intended for administration to neonates, e.g. for treating and/or preventing the above and/or other effects of complications during childbirth. The preparations of the invention may also contain one or more further pharmaceutically acceptable components or ingredients, for instance one or more of the usual ingredients or components for use in infusions for neonates.

Although the invention is not limited to any specific explanation or mechanism, it is assumed that 2-iminobiotin acts by inhibiting neuronal and inducible Nitric Oxide Synthase (NOS I+II), which in turn reduces the (neuronal) formation of nitric oxide and thereby the formation of peroxynitrite which may attack the brain cells or their membranes. In doing so, 2-iminobiotin surprisingly does not show the adverse effect of (also) inhibiting the endothelial form of nitric oxide synthase (eNOS); or at least is more specific in inhibiting nNOS and iNOS relative to eNOS, thereby leaving the cerebral perfusion intact. Another potential mechanism by which 2-iminobiotin may act is by promoting neuronal growth and differentiation, potentially via the insulin-like 1 growth receptor.

Furthermore, although the invention has been described above with reference to 2-iminobiotin (the preferred compound of the invention), it is envisaged that any other available specific neuronal nitric oxide synthase inhibitor e.g. might give comparable results. Some non-limiting examples of such suitable selective nitric oxide synthase inhibitors may include S-benzyl-isothiourea (such as the hydrochloride thereof), α-guanidinoglutaric acid (GGA); L-thiocitrulline, L-$N^5$-(1-iminoethyl)ornithine (L-NIO) (such as the hydrochloride thereof); $N^G$-monomethyl-L-arginine (NMEA); TRIM or pharmaceutically and/or veterinary acceptable salts and/or esters thereof.

The invention will now be illustrated by means of the following Figures and examples, which do not limit the scope of the invention. In the Figures:

FIGS. 1A and 1B show 31P-MR spectra of a representative PLAC treated piglet (FIG. 1A) and a representative 2-IB treated piglet (FIG. 2B) at 24 h post HI.

EXPERIMENTAL PART

Materials and Methods

Following anaesthesia and instrumentation 37 newborn Dutch store piglets (1–3 days old) were subjected to HI by occluding both common carotid arteries with inflatable cuffs and reducing the fraction of inspired oxygen for 60 min. MRS was performed continuously before, during and up to 3 h after start of HI and repeated at 24 h post HI. During hypoxia FiO2 was reduced>on-line=until PCr/Pi had decreased to at least 25% of baseline values. Immediately after HI the piglets received either placebo (PLAC; n=10), ALLO (20 mg/kg iv; n=10), DFO (10 mg/kg iv; n=10) or 2-IB (150 µM i.v.; n=7). Before HI and from 3 to 24 h post HI the piglets were monitored using aEEG for electrical brain activity determination. A neurologic scoring system was used ranging from 4 (normal) to 0 (flat trace). For 1H-MRS a PRESS sequence with CHESS water suppression was used to define a 1.7 ml periventricular voxel (TR 6 s, TE 144 ms, and nt=32 or 64). 31 P— MRS was done using a 4 cm-diameter surface coil for excitation and detection (TR 10 s, nt=32). Peak amplitudes of PCr, Pi, Lac and NAA were determined with time domain fitting procedures (VARPRO). Paired t-tests were used to compare measurements at 24 h versus baseline; repeated ANOVA served to monitor for trends between treatment groups.

Results

Figure 2A:
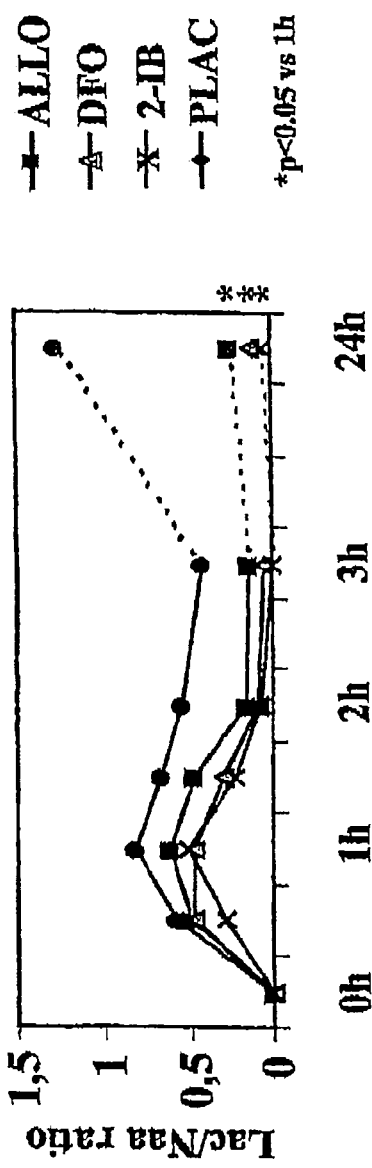
FIGS. 2A and 2B are graphs showing PCr/Pi % (FIG. 2A) and Lac/NAA ratios (FIG. 2B) from normoxia until 24 h post HI in PLAC, ALLO, DFO and 2-IB-treated piglets.
Figure 2B:
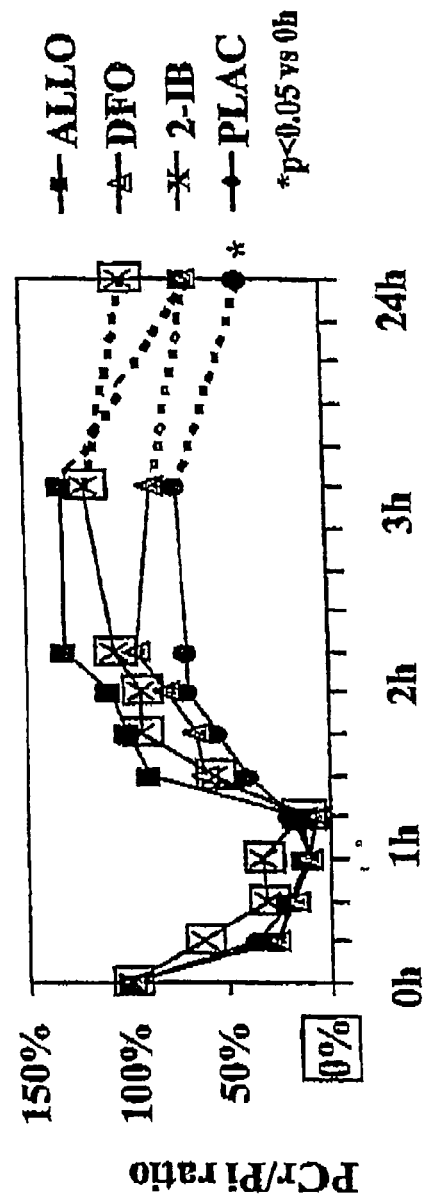
Figure 3:
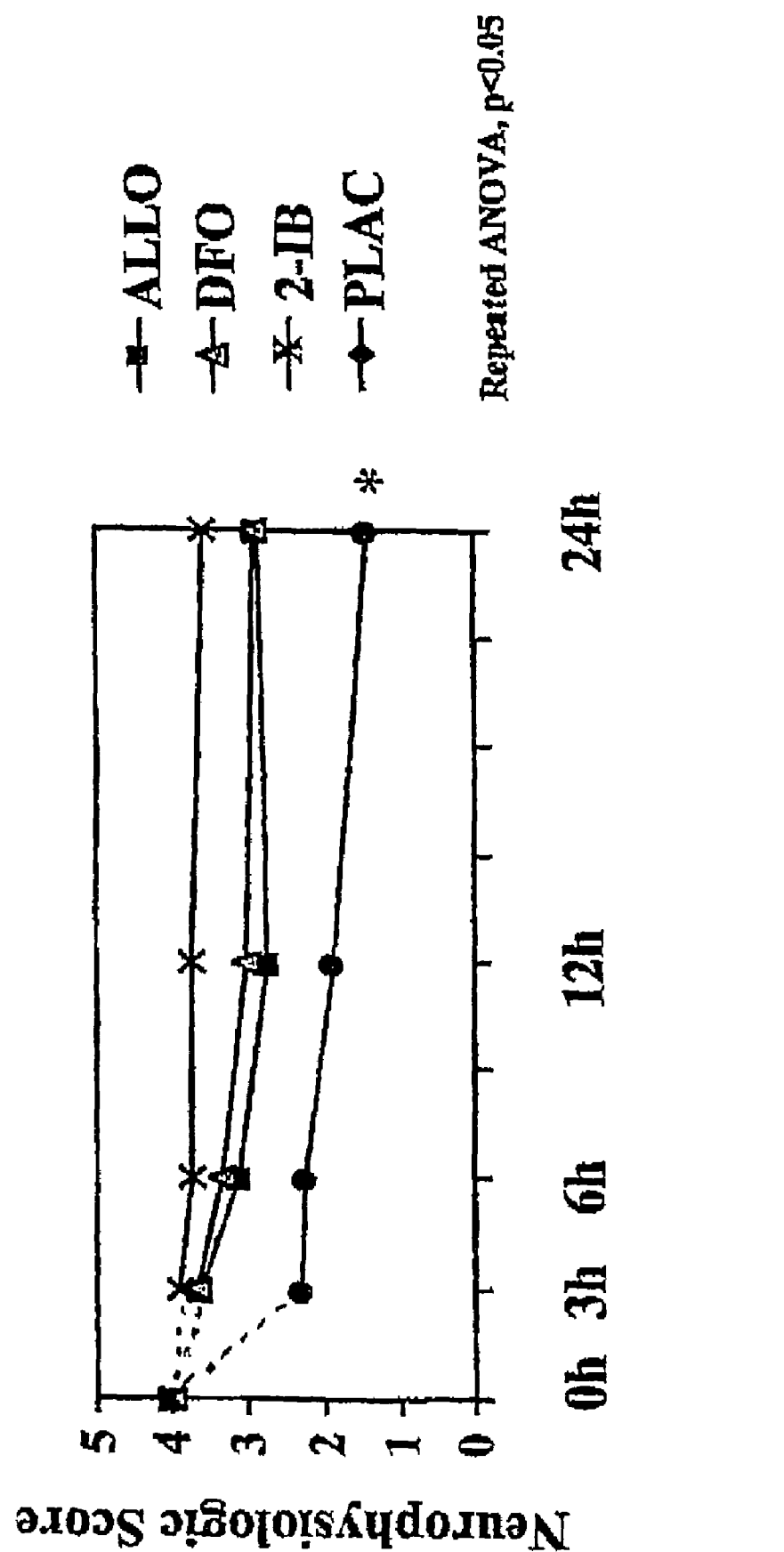
FIG. 3 shows an aEEG for PLAC, ALLO, DFO and 2-IB treated piglets before HI, and at 3, 6, 12 and 24 h post HI.

Three piglets in the PLAC group and 1 piglet in the ALLO group died due to HI complications at respectively 5, 9 and 19 h and 18 h post HI, 1 piglet died at 13 h in the DFO group because of hypovolemic shock and 1 in the 2-IB group due to sepsis. 31 P-MR spectra of a representative PLAC and 2-IB-treated piglet are shown in FIG. 1 at 24 h post HI. Secondary energy failure, defined as a secondary fall in PCr/Pi is observed in the PLAC, but not in the 2-IB piglet. PCr/Pi as percentage of baseline and Lac/NAA ratios from normoxia to 24 h post HI for all treatment groups are presented in FIG. 2. For the 2-IB group 24 h post HI values were identical to baseline values of PCr/Pi and Lac/NAA. For PLAC-treated piglets PCr/Pi was significantly decreased and Lac/NAA significantly increased at 24 h post HI. FIG. 3 shows the neurologic score for all treatment groups. Using repeated ANOVA a significant difference was demonstrated between PLAC and 2-IB, ALLO and DFO (all $p<0.05$).

Histological analysis at 24 h post the hypoxic-ischemic period revealed more alive cells in the 2-IB treated piglets in the brain regions at risk after HI (hippocampus, cortex, striatum and cerebellum), less necrosis and a better preserved structural architecture. Furthermore, immunohistochemistry for nitrotyrosylation in the affected areas (a product being formed by the interaction of peroxynitrite on tyrosine residues) showed no staining in the 2-IB treated piglets, whereas the placebo treated piglets had a considerably level of nitrotyrosylation. This suggests that 2-IB can pass the blood brain barrier after hypoxia-ischemia and that it actually reduces the amount of peroxynitrite that is being formed in brain cells.

CONCLUSION

Whereas ALLO en DFO prevented partly the reduction in PCr/Pi ratios at 24 h post HI, 2-IB preserved completely cerebral energy status at 24 h post HI. 2-IB and to a lesser degree ALLO and DFO prevented increment of Lac/NAA at 24 h post HI and preserved electrical brain activity. Histology confirmed this outcome including less nitrotyrosylation staining in the 2-IB treated animals. We speculate that the remarkable preservation of the cerebral energy status by 2-IB is due to prevention of the formation of peroxynitrite following hypoxia-ischemia in the newborn piglet.

Postnatal Growth Experiments

A study in newborn piglets was performed to identify the potential effects of 2-iminobiotin on postnatal growth. Data from 138 crossbred piglets (originating from 28 litters) were collected on a commercial, Dutch pig farm over the period from 21 Jul. 2001 to 6 May 2003.

In total, 134 piglets were used for the analysis of the data:
   67 piglets were treated with 2-iminobiotin and 67 piglets were treated with saline during the first 24 hours of life (first administration intravenously in v. umbilicalis within five minutes after birth; followed by 6 intraperitoneal administrations; total administration 1.1 mg/kg in 24 h.).
   When applying a model including corrections for sow, parity and birth weight, 2-IB treated piglets showed significantly higher growth rates (in gram/day) than the saline treated piglets:

|  | 2-IB piglets | Saline piglets | p-value |
|---|---|---|---|
| Growth at 10 days | 208 | 188 | 0.018 |
| Growth at weaning | 248 | 225 | 0.004 |
| Growth at 6 weeks | 250 | 230 | 0.007 |

(p-value is p-value for therapy)
(mean values are Least Square Means)

In total 9 piglets (13%) of the 2-IB treated group and 12 piglets (18%) of the saline treated group died, all during the first 10 days of life. Pathology and histology: no adverse effects of the 2-IB treatment were found.

We claim:

1. A method for treating perinatal asphyxia in a human or animal neonate having neonatal asphyxia or being at risk of developing said asphyxia, comprising administering to the mother carrying said neonate an effective amount of a pharmaceutical composition comprising 2-iminobiotin or a salt or ester thereof.

2. The method according to claim 1, wherein the composition is administered intravenously.

3. The method according to claim 1, wherein the composition is administered orally.

4. The method according to claim 1, wherein said neonate has placental insufficiency and/or intra-uterine growth retardation.

* * * * *